(12) United States Patent
Meier et al.

(10) Patent No.: US 7,563,933 B2
(45) Date of Patent: Jul. 21, 2009

(54) METHOD FOR PRODUCING AN ETHYLAMINE

(75) Inventors: Anton Meier, Birkenheide (DE); Johann-Peter Melder, Böhl-Iggelheim (DE); Till Gerlach, Ludwigshafen (DE); Frank Haese, Bollingstedt (DE)

(73) Assignee: BASF Aktiengesellschaft (DE)

( * ) Notice: Subject to any disclaimer, the term of this patent is extended or adjusted under 35 U.S.C. 154(b) by 592 days.

(21) Appl. No.: 10/581,733

(22) PCT Filed: Dec. 22, 2004

(86) PCT No.: PCT/EP2004/014588

§ 371 (c)(1),
(2), (4) Date: Jun. 6, 2006

(87) PCT Pub. No.: WO2005/063681

PCT Pub. Date: Jul. 14, 2005

(65) Prior Publication Data

US 2007/0112218 A1 May 17, 2007

(30) Foreign Application Priority Data

Dec. 23, 2003 (DE) .................................. 103 61 503

(51) Int. Cl.
*C07C 209/16* (2006.01)
(52) U.S. Cl. ....................... 564/480; 564/479
(58) Field of Classification Search .................. None
See application file for complete search history.

(56) References Cited

U.S. PATENT DOCUMENTS

| | | | |
|---|---|---|---|
| 3,275,554 A | 9/1966 | Wagenaar | |
| 3,751,475 A | 8/1973 | van der Voort et al. | |
| 4,690,903 A | 9/1987 | Chen et al. | |
| 4,832,702 A | 5/1989 | Kummer et al. | |
| 5,002,922 A | 3/1991 | Irgang et al. | |
| 5,530,127 A | 6/1996 | Reif et al. | |
| 6,057,442 A * | 5/2000 | Wulff-Doring et al. | 544/106 |
| 6,531,052 B1 | 3/2003 | Frye et al. | |
| 6,723,880 B2 | 4/2004 | Neumann et al. | |
| 2003/0070966 A1 | 4/2003 | Khare | |
| 2003/0113598 A1 | 6/2003 | Chow et al. | |
| 2004/0220428 A1 | 11/2004 | Gerlach et al. | |

FOREIGN PATENT DOCUMENTS

| | | |
|---|---|---|
| CA | 1 242 221 | 9/1988 |
| DE | 21 25 039 | 12/1971 |
| DE | 1 953 263 | 2/1972 |
| DE | 36 11 230 | 10/1987 |
| DE | 102 61 195 | 7/2004 |
| EP | 0 101 254 | 2/1984 |
| EP | 0 211 552 | 2/1987 |
| EP | 0 382 049 | 8/1990 |
| EP | 0 696 572 | 2/1996 |
| EP | 0 963 975 | 12/1999 |
| EP | 1 270 543 | 1/2003 |
| GB | 1 319 495 | 6/1973 |
| JP | 61-074568 | 4/1986 |
| WO | WO-03/020850 | 3/2003 |

OTHER PUBLICATIONS

Eller et al., "Amines, Aliphatic—General Production Methods, 3.1 Production of Alcohols", Ullmann's Encyclopedia of Industrial Chemistry, 6th Edition, 2000 Electronic Release, pp. 1-3.

* cited by examiner

*Primary Examiner*—Brian J Davis
(74) *Attorney, Agent, or Firm*—Connolly Bove Lodge & Hutz LLP

(57) ABSTRACT

Process for preparing an ethylamine by reacting ethanol with ammonia, a primary amine or a secondary amine in the presence of hydrogen and a heterogeneous catalyst, in which a biochemically prepared ethanol (bioethanol) in which the concentration of sulfur and/or sulfur-containing compounds has been reduced beforehand by bringing it into contact with an adsorbent is used.

23 Claims, No Drawings

METHOD FOR PRODUCING AN ETHYLAMINE

RELATED APPLICATIONS

This application is a national stage application (under 35 U.S.C. 371) of PCT/EP2004/014588 filed Dec. 23, 2003, which claims benefit to German application 103 61 503.2 filed Dec. 23, 2003.

DESCRIPTION

The present invention relates to a process for preparing an ethylamine by reacting ethanol with ammonia, a primary amine or a secondary amine in the presence of hydrogen and a heterogeneous catalyst.

The preparation of ethylamines (monoethylamine, diethylamine and triethylamine) is carried out industrially by amination of ethanol by means of ammonia, primary or secondary amines in the presence of hydrogen.

Processes for preparing amines from alcohols are known to those skilled in the art from the literature, e.g. Ullmann's Encyclopedia of Industrial Chemistry, 6th Edition, 2000 electronic release, 'Aliphatic Amines: Production from alcohols'.

The ethanol used can be prepared synthetically, for example by hydration of ethylene. An alternative to synthetic ethanol is biochemically produced ethanol, known as bioethanol, in particular ethanol prepared by fermentation. Bioethanol is prepared from renewable resources and is thus advantageous for ecological reasons. In addition, bioethanol is sometimes cheaper than synthetic ethanol.

However, when bioethanol was used over a typical amination catalyst (e.g. a Cu/Co/Ni catalyst supported on gamma-$Al_2O_3$), the catalyst deactivation was found to be significantly more rapid than was known from the use of synthetic ethanol.

As a result of the more rapid deactivation, the synthesis has to be interrupted more frequently in order to replace the catalyst. This leads to downtimes, increased costs for the catalyst and change in the catalyst and an increased personnel requirement combined with an increased accident risk.

If bioethanol is used in ammination processes, the catalytically active metal surface of the respective heterogeneous catalyst becomes, as has been recognized according to the invention, coated to an increasing extent over time with the sulfur or sulfur compounds introduced via the bioalcohol. This leads to accelerated catalyst deactivation and thus to a significant deterioration in the economic viability of the respective process.

There was therefore the problem of reducing the concentration of or virtually completely removing the sulfur and/or the sulfur-containing compounds, in particular the interfering sulfur-containing compounds, in bioethanol by means of a preceding desulfurization step.

The purification or isolation of biochemically prepared compounds such as bioethanol is frequently carried out by distillation in complicated, multistage processes.

WO-A-2003 020850, US-A1-2003 070966, US-A1-2003 113598 and U.S. Pat. No. B1-6,531,052 concern the removal of sulfur from liquid hydrocarbons (petroleum spirit).

Chemical Abstracts No. 102: 222463 (M.Kh. Annagiev et al., Doklady—Akademiya Nauk Azerbaidzhanskoi SSR, 1984, 40 (12), 53-6) describes the reduction in the concentration of S compounds in technical-grade ethanol (not bioethanol) from 25-30 to 8-17 mg/l by bringing the ethanol into contact with zeolites of the clinoptilolite and mordenite types at room temperature, with the zeolites having been conditioned beforehand at 380° C. for 6 hours and in some cases having been treated with metal salts, in particular $Fe_2O_3$. The S compounds whose concentrations are reduced are $H_2S$ and alkyl thiols (R-SH).

It was an object of the present invention to discover an improved economical process for the catalytic preparation of an ethylamine by reacting ethanol with ammonia, a primary amine or a secondary amine, by means of which corresponding ethylamines, in particular monoethylamine, diethylamine and triethylamine, are obtained in high yield, space-time yield and selectivity.

In particular, the process should make increased catalyst operating lives possible in the synthesis of ethylamines.

(Space-time yields are reported in "amount of product/(catalyst volume·time)" ($kg/(l_{cat.}·h)$) and/or "amount of product/(reactor volume·time)" ($kg/(l_{reator}·h)$).

Accordingly, we have found a process for preparing an ethylamine (or a mixture of ethylamines) by reacting ethanol with ammonia, a primary amine or a secondary amine in the presence of hydrogen and a heterogeneous catalyst, wherein a biochemically prepared ethanol (=bioethanol) in which the concentration of sulfur and/or sulfur-containing compounds has been reduced beforehand by bringing it into contact with an adsorbent is used.

The sulfur-containing compounds are inorganic or organic compounds, in particular symmetrical or unsymmetrical $C_{2-10}$-dialkyl sulfides, particularly $C_{2-6}$-dialkyl sulfides such as diethyl sulfide, di-n-propyl sulfide, diisopropyl sulfide, very particularly dimethyl sulfide, $C_{2-10}$-dialkyl sulfoxides such as dimethyl sulfoxide, diethyl sulfoxide, dipropyl sulfoxide, 3-methylthio-1-propanol and/or S-containing amino acids such as methionine and S-methylmethionine.

Adsorbents used are preferably a silica gel, an activated aluminum oxide, a zeolite having hydrophilic properties, an activated carbon or a carbon molecular sieve.

Examples of silica gels which can be used are silicon dioxide, examples of aluminum oxides which can be used are boehmite, gamma-, delta-, theta-, kappa-, chi- and alpha-aluminum oxide, examples of activated carbons which can be used are carbons produced from wood, peat, coconut shells and also synthetic carbons and carbon blacks produced, for example, from natural gas, petroleum or downstream products, or polymeric organic materials which may also comprise heteroatoms such as nitrogen, and examples of carbon molecular sieves which can be used are molecular sieves produced from anthracite and hard coal by partial oxidation, and are described, for example, in the electronic version of the sixth edition of Ullmann's Encyclopedia of Industrial Chemistry, 2000, Chapter Adsorption, Paragraph 'Adsorbents'.

If the adsorbent is produced as a shaped body, for instance for a fixed-bed process, it can be used in any desired shape. Typical shaped bodies are spheres, extrudates, hollow extrudates, star extrudates, pellets, crushed material, etc., having characteristic diameters of from 0.5 to 5 mm, or monolites and similar structured packing elements (cf. Ullmann's Encyclopedia, Sixth Edition, 2000 Electronic Release, Chapter Fixed-Bed Reactors, Par. 2: Catalyst Forms for Fixed-Bed Reactors).

In the case of the suspension mode, the adsorbent is used in powder form. Typical particle sizes in such powders are 1-100 µm, but it is also possible to use particles significantly smaller than 1 µm, for instance when using carbon black. The filtration in the suspension process can be carried out batchwise, for instance by deep bed filtration. In continuous processes, crossflow filtration, for example, is a possibility.

Preferred adsorbents are zeolites, in particular zeolites from the group consisting of natural zeolites, faujasite, X-zeolite, Y-zeolite, A-zeolite, L-zeolite, ZSM 5-zeolite, ZSM 8-zeolite, ZSM 11-zeolite, ZSM 12-zeolite, mordenite, beta-zeolite, pentasil zeolite and mixtures thereof which contain ion-exchangeable cations.

Such zeolites, including commercial zeolites, are described in Kirk-Othmer Encyclopedia of Chemical Engineering 4th Ed. Vol 16. Wiley, NY, 1995, and also in, for example, Catalysis and Zeolites, J. Weitkamp and L. Puppe, Eds, Springer, Berlin (1999).

It is also possible to use metal organic frameworks (MOFs) (e.g. Li et al., Nature, 402, 1999, pages 276-279).

The cations of the zeolite, e.g. $H^+$ in the case of a zeolite in the H form or $Na^+$ in the case of a zeolite in the Na form, are preferably completely or partly replaced by metal cations, in particular transition metal cations (loading of the zeolites with metal cations).

This can be carried out by, for example, ion exchange, impregnation or evaporation of soluble salts. The metals are, however, preferably applied to the zeolites by ion exchange, since they then have, as recognized according to the invention, a particularly high dispersion and thus a particularly high sulfur absorption capacity. The cation exchange can, for example, be carried out starting from zeolites in the alkali metal, H or ammonium form. Such ion exchange techniques for zeolites are described in detail in Catalysis and Zeolites, J. Weitkamp and L. Puppe, Eds., Springer, Berlin (1999).

Preferred zeolites have a modulus (molar $SiO_2:Al_2O_3$ ratio) in the range from 2 to 1000, in particular from 2 to 100.

Very particular preference is given in the process of the invention to using adsorbents, in particular zeolites, which comprise one or more transition metals, in elemental or cationic form, from groups VIII and IB of the Periodic Table, e.g. Fe, Co, Ni, Ru, Rh, Pd, Os, Ir, Pt, Cu, Ag and/or Au, preferably Ag and/or Cu.

The adsorbent preferably comprises from 0.1 to 75% by weight, in particular from 1 to 60% by weight, particularly preferably from 2 to 50% by weight, very particularly preferably from 5 to 30% by weight, (in each case based on the total mass of the adsorbent) of the metal or metals, in particular the transition metal or transition metals.

Processes for preparing such metal-containing adsorbents are known to those skilled in the art, e.g. from Larsen et al., J. Chem. Phys. 98, 1994 pages 11533-11540 and J. Mol. Catalysis A, 21 (2003), pages 237-246.

In Catalysis and Zeolites, J. Weitkamp and L. Puppe, Eds, Springer, Berlin (1999), ion exchange techniques for zeolites are described comprehensively.

For example, A. J. Hernandez-Maldonado et al. in Ind. Eng. Chem. Res. 42, 2003, pages 123-29, describe a suitable method according to which an Ag—Y-zeolite is prepared by ion exchange of Na—Y-zeolite with an excess of silver nitrate in aqueous solution (0.2 molar) at room temperature over 24-48 hours. After the ion exchange, the solid is isolated by filtration, washed with large amounts of deionized water and dried at room temperature.

In addition, T. R. Felthouse et al., J. of Catalysis 98, pages 411-33 (1986), for example, describe the preparation of the corresponding Pt-containing zeolites from the H forms of Y-zeolite, mordenite and ZSM-5.

The methods disclosed in WO-A2-03/020850 for preparing Cu—Y- and Ag—Y-zeolites by ion exchange from Na—Y-zeolites are also suitable for obtaining the adsorbent preferred for the process of the invention.

Very preferred adsorbents are:

Ag—X-zeolite having an Ag content of from 10 to 50% by weight (based on the total mass of the adsorbent) and Cu—X-zeolite having a Cu content of from 10 to 50% by weight (based on the total mass of the adsorbent).

To carry out the pretreatment of the ethanol according to the invention, the adsorbent is generally brought into contact with the ethanol at temperatures in the range from 0° C. to 200° C., in particular from 10° C. to 50° C.

The contacting with the adsorbent is preferably carried out at an absolute pressure in the range from 1 to 200 bar, in particular from 1 to 5 bar.

It is particularly preferably carried out at room temperature and atmospheric pressure.

In a preferred embodiment of the process of the invention, the ethanol is brought into contact with the adsorbent in the liquid phase, i.e. in liquid form or dissolved or suspended in a solvent or diluent.

Possible solvents are, in particular, those which are able to virtually completely dissolve the ethanol to be purified or are completely miscible therewith and are inert under the process conditions.

Examples of suitable solvents are water, cyclic and alicyclic ethers, e.g. tetrahydrofuran, dioxane, methyl tert-butyl ether, dimethoxyethane, dimethoxypropane, dimethyl diethylene glycol, aliphatic alcohols such as methanol, ethanol, n-propanol or isopropanol, n-butanol, 2-butanol, isobutanol or tert-butanol, carboxylic esters such as methyl acetate, ethyl acetate, propyl acetate or butyl acetate, and also aliphatic ether alcohols such as methoxypropanol.

The concentration of ethanol to be purified in the liquid, solvent-containing phase can in principle be chosen freely and is frequently in the range from 20 to 95% by weight, based on the total weight of the solution/mixture.

One variant of the process of the invention comprises carrying it out in the presence of hydrogen, at atmospheric pressure or under superatmospheric pressure.

The process can be carried out in the gas or liquid phase, in the fixed-bed or suspension mode, with or without backmixing, continuously or batchwise in accordance with the methods known to those skilled in the art (as described, for example, in Ullmann's Encyclopedia, sixth edition, 2000 electronic release, Chapter "Adsorption"). To obtain a very high reduction in the concentration of the sulfur compound, processes having a low degree of backmixing are particularly useful.

The process of the invention makes it possible, in particular, to reduce the concentration of sulfur and/or sulfur-containing compounds in the ethanol by ≧90% by weight, particularly preferably ≧95% by weight, very particularly preferably ≧98% by weight (in each case calculated as S).

The process of the invention makes it possible, in particular, to reduce the concentration of sulfur and/or sulfur-containing compounds in the ethanol to a residual content of <2 ppm by weight, particularly preferably <1 ppm by weight, very particularly preferably from 0 to <0.1 ppm by weight (in each case calculated as S), e.g. determined by the Wickbold method (DIN EN 41).

The pretreatment according to the invention of the ethanol by means of an adsorbent preferably gives an ethanol which has a content of sulfur and/or sulfur-comprising organic compounds in the range from 0 to 2 ppm by weight, preferably from 0 to 1 ppm, particularly preferably from 0 to 0.1 ppm (in each case calculated as S), e.g. determined by the Wickbold method (DIN EN 41), a content of $C_{3-4}$-alkanols in the range from 1 to 5000 ppm by weight, preferably from 5 to 3000 ppm by weight, particularly preferably from 10 to 2000 ppm by weight, a methanol content in the range from 1 to 5000 ppm by weight, preferably from 5 to 3000 ppm by weight, particularly preferably from 10 to 2000 ppm by weight, an ethyl acetate content in the range from 1 to 5000 ppm by weight, preferably from 5 to 3000 ppm by weight, particularly preferably from 10 to 2000 ppm by weight, and a 3-methyl-1-butanol content in the range from 1 to 5000 ppm by weight, preferably from 5 to 3000 ppm by weight, particularly preferably from 10 to 2000 ppm by weight.

The content of $C_{3-4}$-alkanols, methanol, ethyl acetate and 3-methyl-1-butanol is, for example, determined by means of gas chromatography (30 m DB-WAX column, internal diameter: 0.32 mm, film thickness: 0.25 μm, FID, temperature program: 35° C. (5 min.), 10° C./min., heating rate: 200° C. (8 min.).

The bioethanol which is preferably used according to the invention is generally produced from agricultural products such as molasses, cane sugar juice, maize starch or from products of wood saccharification and from sulfite waste liquors by fermentation.

Preference is given to using bioethanol which has been obtained by fermentation of glucose with elimination of $CO_2$ (K. Weissermel and H.-J. Arpe, Industrial Organic Chemistry, Wiley-VCH, Weinheim, 2003, p. 194; Electronic Version of Sixth Edition of Ullmann's Encyclopedia of Industrial Chemistry, 2000, Chapter Ethanol, Paragraph Fermentation). The ethanol is generally isolated from the fermentation broths by distillation methods: Electronic Version of Sixth Edition of Ullmann's Encyclopedia of Industrial Chemistry, 2000, Chapter Ethanol, Paragraph Recovery and Purification.

Processes for preparing an ethylamine by reacting ethanol with ammonia, a primary amine or a secondary amine are known from the literature, e.g. from Ullmann's Encyclopedia of Industrial Chemistry, 6th Edition, 2000 electronic release, 'Aliphatic Amines: Production from alcohols'.

Typical catalysts comprise Cu, Co, Ni and/or Fe, and frequently also noble metals such as Ru, Pt, Pd and Re. The catalysts may be doped, for instance with Ag, Zn, In, Mn, alkali metals and/or Mo.

As support material for these active metals, use is frequently made of aluminum oxide (gamma, delta, theta, alpha, kappa, chi or mixtures thereof), silicon oxide, zeolites, aluminosilicates, etc., and mixtures of these supports.

The catalysts can be produced by known methods, e.g. by precipitation, precipitation onto a support, impregnation.

Particularly preferred heterogeneous catalysts for the ammination of the ethanol which has been pretreated according to the invention comprise, in their catalytically active composition prior to treatment with hydrogen:

from 20 to 85% by weight, preferably from 20 to 65% by weight, particularly preferably from 22 to 40% by weight, of $Al_2O_3$, $TiO_2$, $ZrO_2$ and/or $SiO_2$, from 1 to 30% by weight, particularly preferably from 2 to 25% by weight, of oxygen-containing compounds of copper, calculated as CuO, and from 14 to 70% by weight, preferably from 15 to 50% by weight, particularly preferably from 21 to 45% by weight, of oxygen-containing compounds of nickel, calculated as NiO, with the molar ratio of nickel to copper preferably being greater than 1, in particular greater than 1.2, very particularly preferably from 1.8 to 8.5.

In a further variant, these particularly preferred catalysts further comprise, in their catalytically active composition prior to treatment with hydrogen: from 15 to 50% by weight, particularly preferably from 21 to 45% by weight, of oxygen-containing compounds of cobalt, calculated as CoO.

The oxygen-containing compounds of copper, nickel and if appropriate cobalt, in each case calculated as CuO, NiO and CoO, of the preferred catalysts are generally present in the catalytically active composition (prior to treatment with hydrogen) in a total amount of from 15 to 80% by weight, preferably from 35 to 80% by weight, particularly preferably from 60 to 78% by weight, with the molar ratio of nickel to copper particularly preferably being greater than 1.

Further preferred heterogeneous catalysts for use in the process of the invention are:

catalysts which are disclosed in DE-A-19 53 263 (BASF AG) and comprise cobalt, nickel and copper and aluminum oxide and/or silicon dioxide and have a metal content of from 5 to 80% by weight, in particular from 10 to 30% by weight, based on the total catalyst, with the catalysts comprising, calculated on the basis of the metal content, from 70 to 95% by weight of a mixture of cobalt and nickel and from 5 to 30% by weight of copper and the weight ratio of cobalt to nickel being from 4:1 to 1:4, in particular from 2:1 to 1:2, for example the catalyst which is used in the examples there and has the composition 10% by weight of CoO, 10% by weight of NiO and 4% by weight of CuO on $Al_2O_3$, catalysts which are disclosed in EP-A-382 049 (BASF AG) and whose catalytically active composition before the treatment with hydrogen comprises from 20 to 85% by weight, preferably from 70 to 80% by weight, of $ZrO_2$, from 1 to 30% by weight, preferably from 1 to 10% by weight, of CuO, and from 1 to 40% by weight, preferably from 5 to 20% by weight, each of CoO and NiO, for example the catalysts which are described in loc. cit. on page 6 and have the composition 76% by weight of Zr, calculated as $ZrO_2$, 4% by weight of Cu, calculated as CuO, 10% by weight of Co, calculated as CoO, and 10% by weight of Ni, calculated as NiO, catalysts which are disclosed in EP-A-963 975 (BASF AG) and whose catalytically active composition before treatment with hydrogen comprises from 22 to 40% by weight of $ZrO_2$, from 1 to 30% by weight of oxygen-containing compounds of copper, calculated as CuO, from 15 to 50% by weight of oxygen-containing compounds of nickel, calculated as NiO, with the molar Ni:Cu ratio being greater than 1, from 15 to 50% by weight of oxygen-containing compounds of cobalt, calculated as CoO, from 0 to 10% by weight of oxygen-containing compounds of aluminum and/or manganese, calculated as $Al_2O_3$ and $MnO_2$, respectively, and no oxygen-containing compounds of molybdenum, for example the catalyst A which is disclosed in loc. cit., page 17, and has the composition 33% by weight of Zr, calculated as $ZrO_2$, 28% by weight of Ni, calculated as NiO, 11% by weight of Cu, calculated as CuO and 28% by weight of Co, calculated as CoO, catalysts which are disclosed in EP-A-696 572 (BASF AG) and whose catalytically active composition before reduction with hydrogen comprises from 20 to 85% by weight of $ZrO_2$, from 1 to 30% by weight of oxygen-containing compounds of copper, calculated as CuO, from 30 to 70% by weight of oxygen-containing compounds of nickel, calculated as NiO, from 0.1 to 5% by weight of oxygen-containing compounds of molybdenum, calculated as $MoO_3$, and from 0 to 10% by weight of oxygen-containing compounds of aluminum and/ or manganese, calculated as $Al_2O_3$ and $MnO_2$, respectively, for example the catalyst which is disclosed in loc. cit., page 8, and has the composition 31.5% by weight of $ZrO_2$, 50% by weight of NiO, 17% by weight of CuO and 1.5% by weight of $MoO_3$, catalysts which are described in EP A1-1 270 543 (BASF AG) and comprise at least one element or compound of an element of groups VIII and IB of the Periodic Table, and catalysts which are described in the German patent application No. 10261195.5 of Dec. 20, 2002 (BASF AG) and in whose preparation a precipitation of catalytically active components onto monoclinic, tetragonal or cubic zirconium dioxide has been carried out.

The process of the invention is suitable, for example, for preparing ethylamines of the formula I

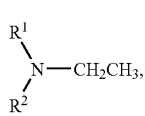

where $R^1$, $R^2$ are each hydrogen (H), alkyl such as $C_{1-200}$-alkyl, cycloalkyl such as $C_{3-12}$-cycloalkyl, hydroxyalkyl such as $C_{1-20}$-hydroxyalkyl, aminoalkyl such as $C_{1-20}$-aminoalkyl, hydroxyalkylaminoalkyl such as $C_{2-20}$-hydroxyalkylaminoalkyl, alkoxyalkyl such as $C_{2-30}$-alkoxyalkyl, dialkylaminoalkyl such as $C_{3-30}$-dialkyl-aminoalkyl, alkylaminoalkyl such as $C_{2-30}$-alkylaminoalkyl, aryl, heteroaryl, aralkyl such as $C_{7-20}$-aralkyl or alkylaryl such as $C_{7-20}$-alkylaryl, or together form a $-(CH_2)_j-X-(CH_2)_k-$ group, X is $CH_2$, $CHR^3$, oxygen (O), sulfur (S) or $NR^3$, $R^3$ is hydrogen (H), alkyl such as $C_{1-4}$-alkyl, alkylphenyl such as $C_{7-40}$-alkylphenyl, and j, k are each an integer from 1 to 4.

The process of the invention is therefore preferably employed for preparing an ethylamine I by reacting the pretreated bioethanol (i.e. the bioethanol which has been pretreated according to the invention) with a nitrogen compound of the formula II

where $R^1$ and $R^2$ are as defined above.

Accordingly, the preparation of the ethylamine I involves purely formal replacement of a hydrogen atom of the nitrogen compound II by the radical $CH_3CH_2-$ with liberation of one molar equivalent of water.

The substituents $R^1$ to $R^3$, the variable X and the indices j, k in the compounds I and II have, independently of one another, the following meanings:

$R^1$, $R^2$:

hydrogen (H), alkyl such as $C_{1-200}$-alkyl, preferably $C_{1-20}$-alkyl, particularly preferably $C_{1-14}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, cyclopentylmethyl, n-heptyl, isoheptyl, cyclohexylmethyl, n-octyl, isooctyl, 2-ethylhexyl, n-decyl, 2-n-propyl-n-heptyl, n-tridecyl, 2-n-butyl-n-nonyl and 3-n-butyl-n-nonyl, in particular $C_{1-4}$-alkyl, cycloalkyl such as $C_{3-12}$-cycloalkyl, preferably $C_{3-8}$-cycloalkyl such as cyclopropyl, cyclobutyl, cyclopentyl, cyclohexyl, cycloheptyl and cyclooctyl, particularly preferably cyclopentyl and cyclohexyl, hydroxyalkyl such as $C_{1-20}$-hydroxyalkyl, preferably $C_{1-8}$-hydroxyalkyl, particularly preferably $C_{1-4}$-hydroxyalkyl such as hydroxymethyl, 1-hydroxyethyl, 2-hydroxy-ethyl, 1-hydroxy-n-propyl, 2-hydroxy-n-propyl, 3-hydroxy-n-propyl and 1-(hydroxymethyl)ethyl, aminoalkyl such as $C_{1-20}$-aminoalkyl, preferably $C_{1-8}$-aminoalkyl such as aminomethyl, 2-aminoethyl, 2-amino-1,1-dimethylethyl, 2-amino-n-propyl, 3-amino-n-propyl, 4-amino-n-butyl, 5-amino-n-pentyl, N-(2-aminoethyl)-2-aminoethyl and N-(2-aminoethyl)aminomethyl, hydroxyalkylaminoalkyl such as $C_{2-20}$-hydroxyalkylaminoalkyl, preferably $C_{3-8}$-hydroxyalkylaminoalkyl such as (2-hydroxyethylamino)methyl, 2-(2-hydroxy-ethylamino)ethyl and 3-(2-hydroxyethylamino)propyl, alkoxyalkyl such as $C_{2-30}$-alkoxyalkyl, preferably $C_{2-20}$-alkoxyalkyl, particularly preferably $C_{2-8}$-alkoxyalkyl such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl and 2-methoxyethyl, particularly preferably $C_{2-4}$-alkoxyalkyl, dialkylaminoalkyl such as $C_{3-30}$-dialkylaminoalkyl, preferably $C_{3-20}$-dialkylaminoalkyl, particularly preferably $C_{3-10}$-N,N-dialkylaminoalkyl such as (N,N-dimethylamino)methyl, (N,N-dibutylamino)methyl, 2-(N,N-dimethylamino)ethyl, 2-(N,N-diethylamino)ethyl, 2-(N,N-dibutylamino)ethyl, 2-(N,N-di-n-propylamino)ethyl, 2-(N,N-diisopropylamino)ethyl, $(R^3)_2N-(CH_2)_q$ (q=1 to 6), very particularly preferably 3-(N,N-dimethylamino)propyl, alkylaminoalkyl such as $C_{2-30}$-alkylaminoalkyl, preferably $C_{2-20}$-alkylaminoalkyl, particularly preferably $C_{2-8}$-alkylaminoalkyl such as methylaminomethyl, 2-(methylamino)ethyl, ethylaminomethyl, 2-(ethylamino)ethyl and 2-(isopropyl-amino)ethyl, $(R^3)HN-(CH_2)_q$ (q=1 to 6), aryl such as phenyl, 1-naphthyl, 2-naphthyl, 1-anthryl, 2-anthryl and 9-anthryl, preferably phenyl, 1-naphthyl and 2-naphthyl, particularly preferably phenyl, heteroaryl such as 2-pyridinyl, 3-pyridinyl, 4-pyridinyl, pyrazinyl, pyrrol-3-yl, imidazol-2-yl, 2-furanyl and 3-furanyl, aralkyl such as $C_{7-20}$-aralkyl, preferably $C_{7-12}$-phenylalkyl such as benzyl, p-methoxybenzyl, 3,4-dimethoxybenzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl, 1-phenethyl and 2-phenethyl, alkylaryl such as $C_{7-20}$-alkylaryl, preferably $C_{7-12}$-alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl and 4-n-propylphenyl, or two radicals together form a $-(CH_2)_j-X-(CH_2)_k-$ group such as $-(CH_2)_3-$, $-(CH_2)_4-$, $-(CH_2)_5-$, —(CH$_2$)$_6$—, —(CH$_2$)—, —(CH$_2$)—O—(CH$_2$)$_2$—, —(CH$_2$)—NR$^3$—(CH$_2$)$_2$—, —(CH$_2$)—CHR$^3$—(CH$_2$)$_2$—, —(CH$_2$)$_2$—O—(CH$_2$)$_2$—, —(CH$_2$)—NR$^3$—(CH$_2$)$_2$—, —(CH$_2$)$_2$—CHR$^3$—(CH$_2$)$_2$—, —CH$_2$—O—(CH$_2$)$_3$—, —CH$_2$—NR$^3$—(CH$_2$)$_3$—, R$^3$:
hydrogen (H),
alkyl, in particular C$_{1-4}$-alkyl such as methyl, ethyl, n-propyl, isopropyl, n-butyl, isobutyl, sec-butyl and tert-butyl, preferably methyl and ethyl, particularly preferably methyl,
alkylphenyl, in particular C$_{7-40}$-alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2-, 3-, 4-nonylphenyl, 2-, 3-, 4-decylphenyl, 2,3-, 2,4-, 2,5-, 3,4-, 3,5-dinonylphenyl, 2,3-, 2,4-, 2,5-, 3,4- and 3,5-didecylphenyl, X:
CH$_2$, CHR$^3$, oxygen (O), sulfur (S) or NR$^3$, preferably CH$_2$, NH and O, j:
an integer from 1 to 4 (1, 2, 3 or 4), preferably 1 and 2, and k:
an integer from 1 to 4 (1, 2, 3 or 4), preferably 1 and 2.

As aminating agent in the hydrogenated amination of the bioethanol in the presence of hydrogen, it is possible to use either ammonia or primary or secondary, aliphatic or cycloaliphatic or aromatic amines.

When ammonia is used as aminating agent, the alcoholic hydroxyl group is firstly converted into a primary amino group (—NH$_2$). The primary ethylamine formed in this way can react with further ethanol to form the corresponding secondary amine (diethylamine) and this can in turn react with further alcohol to form the corresponding tertiary amine (triethylamine). Depending on the composition of the reaction batch or the feed stream (in the case of continuous operation) and depending on the reaction conditions employed, viz. pressure, temperature, catalyst, reaction time (space velocity over the catalyst), primary, secondary or tertiary ethylamines can be prepared preferentially in this way, depending on what is wanted.

Like ammonia, primary or secondary amines can be used as aminating agents.

These aminating agents are preferably used for preparing unsymmetrically substituted dialkylamines or trialkylamines such as ethyldiisopropylamine and ethyldicyclohexylamine.

For example, the following monoalkylamines and dialkylamines are used as aminating agents: methylamine, dimethylamine, ethylamine, diethylamine, n-propylamine, di-n-propylamine, isopropylamine, diisopropylamine, isopropylethylamine, n-butylamine, di-n-butylamine, s-butylamine, di-s-butylamine, isobutylamine, n-pentylamine, s-pentylamine, isopentylamine, n-hexylamine, s-hexylamine, isohexylamine, cyclohexylamine, aniline, toluidine, piperidine, morpholine and pyrrolidine.

Amines which are particularly preferably prepared using the process of the invention are, for example, monoethylamine (from ethanol and ammonia), diethylamine (from ethanol and monoethylamine), triethylamine (from ethanol and diethylamine), monoethylamine/diethylamine/triethylamine mixture (from ethanol and ammonia) and dimethylethylamine (from ethanol and dimethylamine).

The aminating agent can be used in stoichiometric, substoichiometric or superstoichiometric amounts relative to the alcoholic hydroxyl group to be aminated.

In the case of amination using primary or secondary amines, the amine is preferably used in an approximately stoichiometric amount or slightly superstoichiometric amount per mole of alcoholic hydroxyl group.

Ammonia itself is generally used in a 1.5- to 250-fold, preferably 2- to 100-fold, in particular 2- to 10-fold, molar excess per mole of alcoholic hydroxyl group to be reacted.

Larger excesses both of ammonia and of primary or secondary amines are possible.

The process of the invention can be carried out batchwise or preferably continuously as follows, with the catalyst preferably being present as a fixed bed in the reactor. However, the embodiment as a fluidized-bed reaction with upward and downward swirling motion of the catalyst material is likewise possible.

The amination can be carried out in the liquid phase or in the gas phase. Preference is given to a fixed-bed process in the gas phase.

When the amination is carried out in the liquid phase, the starting materials (alcohol plus ammonia or amine) are simultaneously passed in the liquid phase together with hydrogen over the catalyst, which is usually present in a preferably externally heated fixed-bed reactor, at pressures of generally from 5 to 30 MPa (50-300 bar), preferably from 5 to 25 MPa, particularly preferably from 15 to 25 MPa, and temperatures of generally from 80 to 300° C., preferably from 120 to 270° C., particularly preferably from 130 to 250° C., in particular from 170 to 230° C. Operation in either the downflow mode or the upflow mode is possible. The space velocity of the catalyst is generally in the range from 0.05 to 5 kg, preferably 0.1 to 2 kg, particularly preferably from 0.2 to 0.6 kg, of alcohol per liter of catalyst (bed volume) and hour. If appropriate, the starting materials can be diluted with a suitable solvent such as tetrahydrofuran, dioxane, N-methylpyrrolidone or ethylene glycol dimethyl ether. It is advantageous to heat the reactants before they are fed into the reaction vessel, preferably to the reaction temperature.

When the amination is carried out in the gas phase, the gaseous starting materials (alcohol plus ammonia or amine) are passed in a gas stream, preferably hydrogen, which is sufficiently large for vaporization over the catalyst in the presence of hydrogen at pressures of generally from 0.1 to 40 MPa (1 to 400 bar), preferably from 0.1 to 10 MPa, particularly preferably from 0.1 to 7 MPa. The temperatures for the amination are generally from 80 to 300° C., preferably from 120 to 270° C., particularly preferably from 160 to 250° C. It is possible for the gas stream to flow into the fixed bed of catalyst either from above or from below. The gas stream required is preferably obtained by means of recycle gas operation.

The space velocity of the catalyst is generally in the range from 0.01 to 2 kg, preferably from 0.05 to 0.5 kg, of alcohol per liter of catalyst (bed volume) and hour.

The hydrogen is generally fed to the reaction in an amount of from 5 to 400 l, preferably from 50 to 200 l, per mole of alcohol component, with the liter figures being in each case based on S.T.P.

Both when working in the liquid phase and when working in the gas phase, it is possible to employ higher temperatures and higher total pressures. The pressure in the reaction vessel, which is the sum of the partial pressures of the aminating agent, of the alcohol and of the reaction products formed and also, if appropriate, of the solvent used at the temperatures indicated, is advantageously increased to the desired reaction pressure by injection of hydrogen.

Both when carrying out the process continuously in the liquid phase and when carrying it out continuously in the gas phase, the excess amminating agent can be circulated together with the hydrogen.

If the catalyst is present as a fixed bed, it can be advantageous in terms of the selectivity of the reaction to mix the shaped catalyst bodies in the reactor with inert packing elements, i.e. to "dilute" it. The proportion of packing elements in such catalyst preparations can be from 20 to 80, particularly from 30 to 60 and in particular from 40 to 50, parts by volume.

The water of reaction formed during the course of the reaction (in each case one mole per mole of alcohol group reacted) generally does not adversely affect the conversion, the reaction rate, the selectivity and the operating life of the catalyst and is therefore advantageously removed from the reaction product only in the work-up of the latter, e.g. by distillation.

After the product mixture from the reaction has advantageously been depressurized, the excess amminating agent and the hydrogen are removed and the ammination products obtained (ethylamines) are purified by distillation or rectification, liquid extraction or crystallization. The excess amminating agent and the hydrogen are advantageously returned to the reaction zone. The same applies to any incompletely reacted alcohol.

The amines prepared using the process of the invention are suitable, inter alia, as intermediates in the production of fuel additives (U.S. Pat. No. 3,275,554; DE-A-21 25 039 and DE-A-36 11 230), surfactants, drugs and crop protection agents, hardeners for epoxy resins, catalysts for polyurethanes, intermediates for preparing quaternary ammonium compounds, plasticizers, corrosion inhibitors, synthetic resins, ion exchangers, textile assistants, dyes, vulcanization accelerators and/or emulsifiers

EXAMPLES

I) Ammination of Bioethanol and Pretreated (according to the invention) Bioethanol using Ammonia When bioethanol having a sulfur content of 0.5-2 ppm was used for the synthesis of ethylamines (monoethylamine, diethylamine and triethylamine) by reaction with ammonia at 150-250° C. and 60 bar over an ammination catalyst (3.4% by weight of Cu, 8.3% by weight of Co, 8.3% by weight of Ni supported on gamma-$Al_2O_3$) the catalyst deactivation observed was significantly faster than is the case when synthetic ethanol having a sulfur content of <0.1 ppm is used.

When the sulfur content of samples of the deactivated synthesis catalyst which had been removed from the reactor after use of bioethanol was measured, it was found to have increased considerably:

|  | Fresh | After removal |
|---|---|---|
| S content/ppm | 25 | 670 |

The determination of the S content of the input and output was carried out (in all examples) coulometrically (DIN 51400 Part 7) with a detection limit of 2 ppm.

0.5-2 ppm of sulfur were detected in the bioethanol feed used in the ammination. More precise analyses indicated that a typical organic sulfur compound in the bioethanol is dimethyl sulfide. In addition, sulfate sulfur species and also possibly further organic sulfur species, e.g. $C_{2-10}$-dialkyl sulfides, $C_{2-10}$-dialkyl sulfoxides, 3-methylthio-1-propanol and/or S-containing amino acids, are present in the bioethanol.

The example shows that the sulfur compounds present in the bioethanol, in particular the organic sulfur compounds, especially dimethyl sulfide, have led to accelerated catalyst deactivation.

II) Treatment of Bioethanol According to the Invention by Bringing it into Contact with an Adsorbent Preparation of Ag-zeolites

Example 1

Ag-zeolite Powder

A solution of $AgNO_3$ (7.71 g of $AgNO_3$ in water, 200 ml total) was placed in a glass beaker, the zeolite (ZSM-5, 200 g, molar $SiO_2/Al_2O_3$ ratio=40-48, Na form) was slowly added while stirring and the mixture was stirred at room temperature for 2 hours. The adsorbent was then filtered off via a fluted filter. The adsorbent was subsequently dried at 120° C. for 16 hours in a dark drying oven. The adsorbent comprised 2.1% by weight of Ag (based on the total mass of the adsorbent).

Example 2

Ag-zeolite Shaped Bodies

A solution of $AgNO_3$ (22.4 g in water, 100 ml total) was placed in a glass beaker. The zeolite (65 g of molar sieve 13× in the form of spheres having a diameter of 2.7 mm, molar $SiO_2/Al_2O_3$ ratio=2, Na form) was placed in the apparatus. 400 ml of water were then introduced and were circulated by pumping at room temperature in a continuous plant. The silver nitrate solution was added dropwise over a period of 1 hour. The mixture was then circulated by pumping overnight (23 h). The adsorbent was then washed free of nitrate with 12 liters of deionized water and was subsequently dried overnight at 120° C. in a dark drying oven. The adsorbent comprised 15.9% by weight of Ag (based on the total mass of the adsorbent).

Example A

All ppm figures in this document are by weight.

To test the desulfurization, 10 g of the adsorbent (cf. the table below) were in each case baked overnight at 150° C. in a drying oven to remove adsorbed water. After the solid had cooled, it was taken from the drying oven and 300 ml of ethanol (absolute ethanol, >99.8%, source: Riedel de Haën) were poured over it. About 17 ppm of dimethyl sulfide (corresponds to about 9 ppm of sulfur) had been added to the ethanol, since preliminary experiments showed that dimethyl sulfide is a sulfur compound representative of the organic sulfur compounds present in bioethanol.

The Ag/ZSM-5 adsorbent was prepared by ion exchange of the Na-ZSM-5 with an aqueous $AgNO_3$ solution (50 g of ZSM-5, 1.94 g of $AgNO_3$, 50 ml of impregnation solution). A commercially available ZSM-5 (molar $SiO_2/Al_2O_3$ ratio=40-48, Na form, ALSI-PENTA®) was used for this purpose. The catalyst was subsequently dried at 120° C.

The Ag/$SiO_2$ adsorbent was prepared by impregnating $SiO_2$ (BET about 170 m²/g, $Na_2O$ content: 0.4% by weight)

with an aqueous AgNO$_3$ solution (40 g of SiO$_2$, 1.6 g of AgNO$_3$, 58 ml of impregnation solution). The catalyst was subsequently dried at 120° C. and calcined at 500° C.

The Ag/Al$_2$O$_3$ adsorbent was prepared by impregnating gamma-Al$_2$O$_3$ (BET about 220 m$^2$/g) with an aqueous AgNO$_3$ solution (40 g of Al$_2$O$_3$, 1.6 g of AgNO$_3$, 40 ml of impregnation solution). The catalyst was subsequently dried at 120 ° C. and calcined at 500° C.

The ethanol/adsorbent suspension was transferred to a 4-neck glass flask into which nitrogen was passed for about 5 minutes to make it inert. The flask was subsequently closed and the suspension was stirred at room temperature for 5 hours. After the experiment, the adsorbent was filtered off by means of a fluted filter. The sulfur content of the filtrate and, if appropriate, of the adsorbent was determined coulometrically:

| | S content/ppm | | | |
|---|---|---|---|---|
| Adsorbent | Input | Output | Fresh adsorbent | Laden adsorbent |
| Ag/ZSM-5 | 9 | <2 | 25 | 230 |
| ZSM-5 | 9 | 4 | n.d. | n.d. |
| Ag/Al$_2$O$_3$ | 9 | 2 | n.d. | n.d. |
| Ag/SiO$_2$ | 9 | 4 | n.d. | n.d. |

(n.d. = not determined)

The table shows that the silver-laden zeolite in particular was able to reduce the sulfur content to values below the detection limit (=2 ppm).

After the same Ag/ZSM-5 sample had been used three times, <2 ppm of sulfur were detected in the ethanol after carrying out the experiment.

Even in the case of the adsorbents in which silver had been applied to other supports such as Al$_2$O$_3$ or SiO$_2$, desulfurization was observed. Even the undoped zeolite led to some removal of sulfur from the ethanol. The best result was obtained using the silver-doped zeolite.

Other materials such as Cu/ZnO/Al$_2$O$_3$ catalysts or Ni catalysts were also suitable for removing S from bioethanol, but not as good as the silver-doped zeolite even when the treatment was carried out at elevated temperature with addition of hydrogen.

Examples B

Example B1

To test the desulfurization, 20 g of the pulverulent adsorbent Ag-ZSM5, 2.1% by weight of Ag, were used (cf. Example 1) and 300 ml of ethanol (absolute ethanol, >99.8%, source: Riedel de Haën) were poured over it. About 175 ppm of dimethyl sulfide (>99%, Merck) (corresponds to about 90 ppm of sulfur) had been added to the ethanol, since preliminary experiments showed that dimethyl sulfide is a sulfur compound representative of the organic sulfur compounds present in bioethanol. The ethanol/adsorbent suspension was transferred to a closed 4neck glass flask. The suspension was stirred at room temperature and atmospheric pressure. After the experiment, the adsorbent was filtered off via a fluted filter. The sulfur content of the input, filtrate and, if appropriate, the adsorbent was determined coulometrically. The same Ag-ZSM5 sample was used another three times:

| Use | Residence time Hours | Input S ppm | Output S ppm | Laden adsorbent S ppm |
|---|---|---|---|---|
| 1 | 5 | 84 | <2 | 1300 |
| 2 | 24 | 84 | <2 | 2800 |
| 3 | 24 | 95 | 10 | 4600 |
| 4 | 24 | 97 | 29 | 5900 |

Example B2

To test the desulfurization, 300 ml of ethanol (absolute ethanol, >99.8%, Riedel de Haën) were poured over pulverulent desulfurization material. About 175 ppm of dimethyl sulfide (>99%, Merck) (corresponds to about 90 ppm of sulfur) had been added to the ethanol. The ethanol/adsorbent suspension was transferred to a closed 4-neck glass flask. The suspension was stirred at room temperature and atmospheric pressure for 24 hours. After the experiment, the adsorbent was filtered off via a fluted filter. The sulfur content of the input, filtrate and, if appropriate, the adsorbent was determined coulometrically.

| Adsorbent | Adsorbent % by weight | Input S ppm | Output S ppm | Laden adsorbent S ppm |
|---|---|---|---|---|
| 40 CuO/40 ZnO/20 Al$_2$O$_3$, in % by weight | 8.5 | 84 | 64 | 22 |
| 17 NiO/15 SiO$_2$/5 Al$_2$O$_3$/ 5 ZrO$_2$, in % by weight | 8.5 | 95 | 58 | 9 |
| 5% by weight Pd/C | 2.5 | 100 | 39 | 2300 |
| 2nd use of the Pd/C adsorbent | | 97 | 60 | 3000 |

The materials CuO—ZnO/Al$_2$O$_3$ and NiO/SiO$_2$/Al$_2$O$_3$/ZrO$_2$ are suitable for desulfurization, but are not as good as, for example, a silver-doped zeolite, even when the treatment was carried out at elevated temperature and with addition of hydrogen. If palladium on carbon is used, sulfur is taken up from ethanol.

Example B3

To test the adsorbent, a continuous fixed-bed plant having a total volume of 192 ml was charged with 80.5 g of Ag-13X spheres (15.9% by weight of Ag, 2.7 mm spheres, described in Example 2). About 80 ppm of dimethyl sulfide (>99%, Merck) (corresponds to about 40 ppm of sulfur) were added to the feed ethanol (absolute ethanol, >99.8%, Riedel de Haën). The feed was passed over the adsorbent in the upflow mode. During sampling, the sample flask was always cooled in an ice/salt mixture.

| Time of operation | Cumulative loading (ppm of S/g of adsorbent) | Input S ppm | Output S ppm |
|---|---|---|---|
| 24 | 934 | 38 | <2 |
| 48 | 1623 | 41 | <2 |
| 72 | 2222 | 42 | <2 |

The determination of sulfur in the input and output was carried out (in all examples) coulometrically (DIN 51400 Part 7) with a detection limit of 2 ppm.

Example B4

To test the desulfurization, 500 ml of ethanol (absolute ethanol, >99.8%, Riedel de Haën) were in each case poured over 4 of the adsorbent (cf. the table below). About 390 ppm of dimethyl sulfide (>99%, Merck) (corresponds to about 200 ppm of sulfur) had been added to the ethanol.

The preparation of Ag-13X is described in Example 1. CBV100 and CBV720 are zeolite-Y systems. The doping with metals was carried out by cation exchange in a manner analogous to Example 1 using $AgNO_3$ or $CuNO_3$ solutions. The Cu-CPV720 was subsequently calcined at 450° C. in $N_2$.

The ethanol/adsorbent suspension was transferred to a 4-neck glass flask and stirred at room temperature under atmospheric pressure for 24 hours. After the experiment, the adsorbent was filtered off via a fluted filter. The sulfur content of the filtrate and, if appropriate, of the adsorbent was determined coulometrically:

| Adsorbent | Form | S contents/ppm | | |
|---|---|---|---|---|
| | | Input | Output | Laden adsorbent |
| None | — | 200 | 170 | — |
| Ag-13X | Spheres (2.7 mm) | 200 | 96 | n.d. |
| Ag-CBV100 | Powder | 190 | 13 | 18000 |
| Ag-CBV720 | Powder | 190 | 77 | n.d. |
| Cu-CBV720 | Powder | 190 | 97 | 390 |

(n.d. = not determined)

The table shows that both silver-doped zeolites and copper-doped zeolites are able to desulfurize ethanol.

EXAMPLE

Various commercial bioethanol grades were analyzed to determine their sulfur content

| | Bio-EtOH 1 | Bio-EtOH 2 | Bio-EtOH 3 | Bio-EtOH 4 | Bio-EtOH 5 | Bio-EtOH 6 | Bio-EtOH 7 |
|---|---|---|---|---|---|---|---|
| Total S (ppm by weight) | 0.6 | 1 | 0.6 | 8 | 2 | 49 | 2 |
| Sulfate S (ppm by weight) | 0.33 | 0.43 | 0.2 | n.d. | 0.9 | 6 | 2 |

Total S = Total sulfur, determined coulometrically in accordance with DIN 51400 Part 7
Total sulfur contents ≦2 ppm were determined by the Wickbold method (DIN EN 41)
Sulfate S = Sulfate sulfur, determined by ion chromatography using a method analogous to that of EN ISO 10304-2

The invention claimed is:

1. A process for preparing an ethylamine which comprises reacting ethanol with ammonia, a primary amine or a secondary amine in the presence of hydrogen and a heterogeneous catalyst, wherein a biochemically prepared ethanol (bioethanol) in which the concentration of sulfur and/or sulfur-comprising compounds has been reduced beforehand by bringing it into contact with an adsorbent is used and the adsorbent is a silica gel, an aluminum oxide, a zeolite, an activated carbon or a carbon molecular sieve and comprises one or more transition metals, in elemental or cationic form, from groups VIII and/or IB of the Periodic Table.

2. The process according to claim 1, for preparing monoethylamine, diethylamine and/or triethylamine by reacting ethanol with ammonia.

3. The process according to claim 1, wherein an ethanol prepared by fermentation is used.

4. The process according to claim 1, wherein ethanol in which the concentration of $C_{2-10}$-dialkyl sulfides, $C_{2-10}$-dialkyl sulfoxides, 3-methylthio-1-propanol and/or S-comprising amino acids has been reduced beforehand by bringing it into contact with an adsorbent is used.

5. The process according to claim 1, wherein ethanol in which the concentration of dimethyl sulfide has been reduced beforehand by bringing it into contact with an adsorbent is used.

6. The process according to claim 1, wherein the zeolite is a zeolite from the group consisting of natural zeolites, faujasite, X-zeolite, Y-zeolite, A-zeolite, L-zeolite, ZSM 5-zeolite, ZSM 8-zeolite, ZSM 11-zeolite, ZSM 12-zeolite, mordenite, beta-zeolite, pentasil zeolite, metal organic frameworks (MOF) and mixtures thereof which contain ion-exchangeable cations.

7. The process according to claim 1, wherein the zeolite has a molar $SiO_2/Al_2O_3$ ratio in the range from 2 to 100.

8. The process according to any of claim 1, wherein cations of the zeolite have been completely or partly replaced by metal cations.

9. The process according to claim 1, wherein the adsorbent comprises silver and/or copper.

10. The process according to claim 1, wherein the adsorbent comprises from 0.1 to 75% by weight of the metal or metals.

11. The process according to claim 1, wherein the prior contacting of the ethanol with the adsorbent has been carried out at a temperature in the range from 10 to 200° C.

12. The process according to claim 1, wherein the prior contacting of the ethanol with the adsorbent has been carried out at an absolute pressure in the range from 1 to 200 bar.

13. The process according to claim 1, wherein the concentration of sulfur and/or sulfur-comprising compound has been reduced by ≧ 90% by weight (calculated as S) by the prior contacting of the ethanol with the adsorbent.

14. The process according to claim 1, wherein the concentration of sulfur and/or sulfur-comprising compound has been reduced by ≧ 95% by weight (calculated as S) by the prior contacting of the ethanol with the adsorbent.

15. The process according to claim 1, wherein the concentration of sulfur and/or sulfur-comprising compound has been reduced by ≧ 98% by weight (calculated as S) by the prior contacting of the ethanol with the adsorbent.

16. The process according to claim 1, wherein the concentration of sulfur and/or sulfur-comprising compound has been reduced to < 2 ppm by weight (calculated as S) by the prior contacting of the ethanol with the adsorbent.

17. The process according to claim 1, wherein the concentration of sulfur and/or sulfur-comprising compound has been reduced to < 1 ppm by weight (calculated as S) by the prior contacting of the ethanol with the adsorbent.

18. The process according to claim 1, wherein the concentration of sulfur and/or sulfur-comprising compound has been reduced to < 0.1 ppm by weight (calculated as S) by the prior contacting of the ethanol with the adsorbent.

19. The process according to claim 1, wherein the prior contacting of the ethanol with the adsorbent has been carried out in the absence of hydrogen.

20. The process according to claim 1, wherein the ethanol used has previously been brought into contact with the adsorbent in the liquid phase.

21. The process according to claim 1, wherein the reaction of the ethanol with ammonia, a primary amine or a secondary amine is carried out at a temperature in the range from 80 to 300° C.

22. The process according to claim 1, wherein the reaction of the ethanol with ammonia, a primary amine or a secondary amine is carried out in the liquid phase at pressures in the range from 5 to 30 MPa or in the gas phase at pressures in the range from 0.1 to 40 MPa.

23. The process according to claim 1, wherein the heterogeneous catalyst used for the reaction of the ethanol with ammonia, a primary amine or a secondary amine is a hydrogenation/dehydrogenation catalyst comprising a metal of group VIII and/or IB of the Periodic Table.

* * * * *